United States Patent
Asada et al.

[11] Patent Number: 5,811,610
[45] Date of Patent: Sep. 22, 1998

[54] TRICYCLOCARBOXYLATE, METHOD FOR PREPARING THE SAME AND PERFUME COMPRISING THE SAME

[75] Inventors: Takahiro Asada; Yoshiharu Ataka; Junji Koshino; Hideto Takase, all of Wakayama, Japan

[73] Assignee: Kao Corporation, Tokyo, Japan

[21] Appl. No.: 875,396

[22] PCT Filed: Nov. 27, 1996

[86] PCT No.: PCT/JP96/03483

§ 371 Date: Jul. 30, 1997

§ 102(e) Date: Jul. 30, 1997

[87] PCT Pub. No.: WO97/19906

PCT Pub. Date: Jun. 5, 1997

[30] Foreign Application Priority Data

Nov. 30, 1995 [JP] Japan ................................ 7-338287

[51] Int. Cl.[6] ....................................................... C07C 5/09
[52] U.S. Cl. ................................................................. 585/435
[58] Field of Search .................................................. 585/435

[56] References Cited

FOREIGN PATENT DOCUMENTS

| 0 363 218 | 4/1990 | European Pat. Off. . |
| 2 478 084 | 9/1981 | France . |
| B-86-40658 | 7/1983 | Japan . |

OTHER PUBLICATIONS

H. Koch and W. Heaf, Liebigs. Ann. Chem., 638, 111 (1960).
J. Am.Chem.Soc., vol. 79, 1095 (1957).
Organic Syntheses, Coll., vol. 4, 238 (1963).

*Primary Examiner*—Terressa Mosley
*Attorney, Agent, or Firm*—Oblon, Spivak, McClelland, Maier & Neustadt, P.C.

[57] ABSTRACT

A tricyclo[$5.2.1.0^{2,6}$]deca-8-ene-2-carboxylate; a method preparing the same; a method for preparing the tricyclo [$5.2.1.0^{2,6}$]decane-2-carboxylate by reducing a double bond of the tricyclo[$5.2.1.0^{2,6}$]deca-8-ene-2-carboxylate; and a perfume comprising the tricyclo[$5.2.1.0^{2,6}$]decane-2-carboxylate.

5 Claims, 1 Drawing Sheet

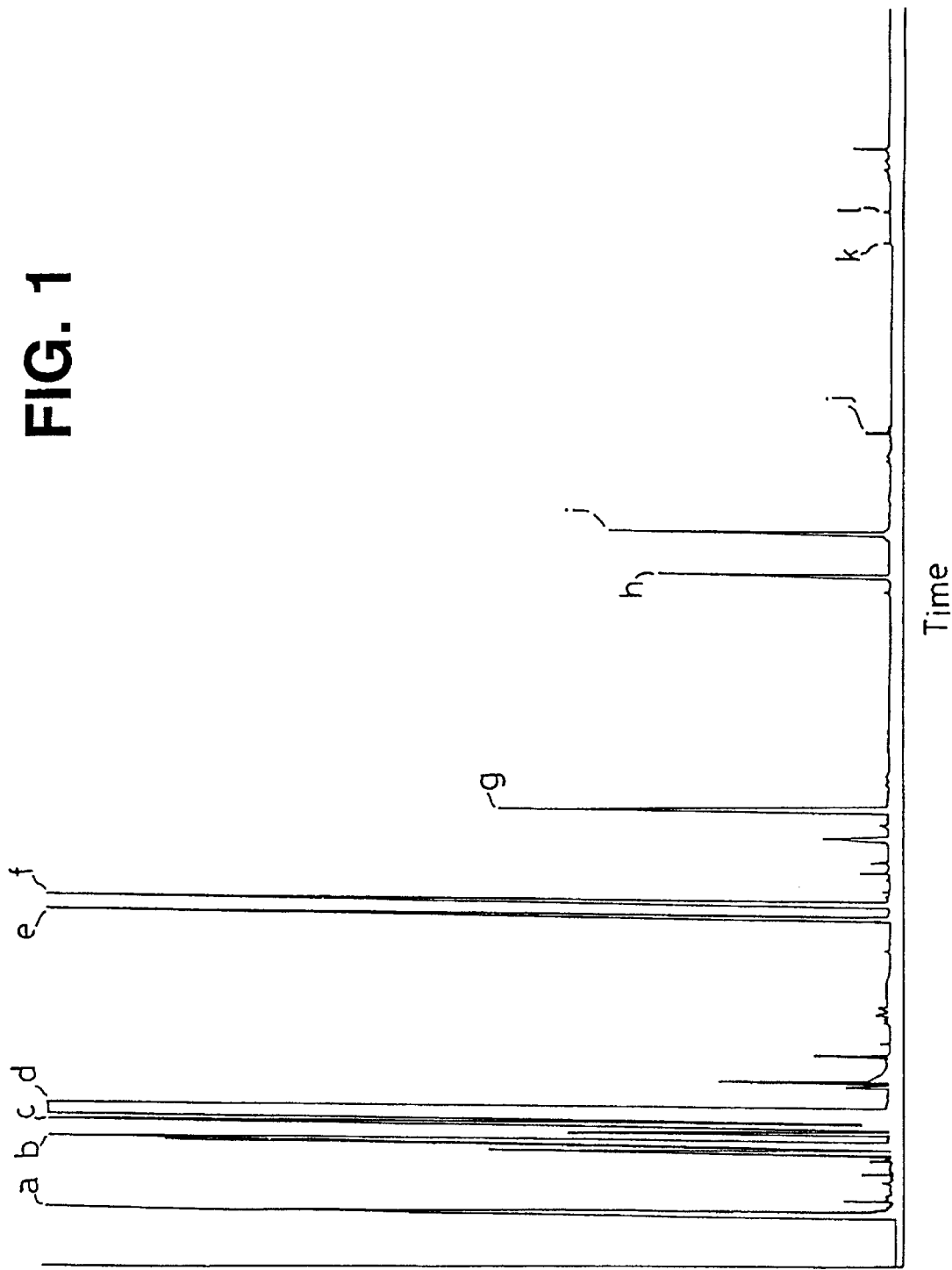

TRICYCLOCARBOXYLATE, METHOD FOR PREPARING THE SAME AND PERFUME COMPRISING THE SAME

TECHNICAL FIELD

The present invention relates to tricyclo[$5.2.1.0^{2,6}$]deca-8-ene-2-carboxylate represented by the formula (I) which is a novel tricyclic carboxylate, a method for preparing the same, and a perfume comprising the same. Also, the present invention relates to tricyclo[$5.2.1.0^{2,6}$]decane-2-carboxylate represented by the formula (III).

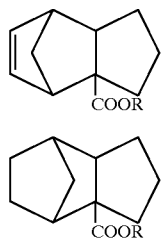

In the formulae (I) and (III), R is an alkyl group having 1 to 3 carbon atoms.

The carboxylate represented by the formula (I) is useful not only as a perfume but also as an intermediate compound for the preparation of a perfume. That is, the carboxylate represented by the formula (I) is useful as an intermediate of tricyclo[$5.2.1.0^{2,6}$]decane-2-carboxylate represented by the formula (III) which is a very useful compound as perfume as disclosed in Japanese Examined Patent Publication No. 61-1014.

BACKGROUND ART

Conventionally, tricyclo[$5.2.1.0^{2,6}$]decane-2-carboxylate (III) represented by the formula (III) described in the following schemes 1 and 2, which is very useful as a perfume, has been prepared by esterifying the corresponding carboxylic acid represented by the formula (IV) obtained by the Koch carboxylation reaction of dihydrodicyclopentadiene as shown by the following scheme 1 (Japanese Examined Patent Publication No. 61-1014), or by contacting tricyclo[$5.2.1.0^{2,6}$]deca-8-yl-formate with an inorganic strongly acidic catalyst as shown by the following scheme 2 (Japanese Examined Patent Publication No. 61-40658).

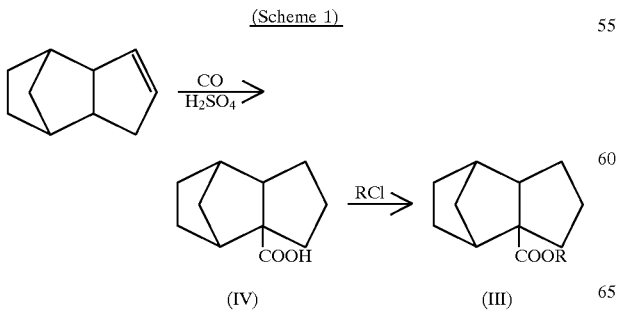

(Scheme 1)

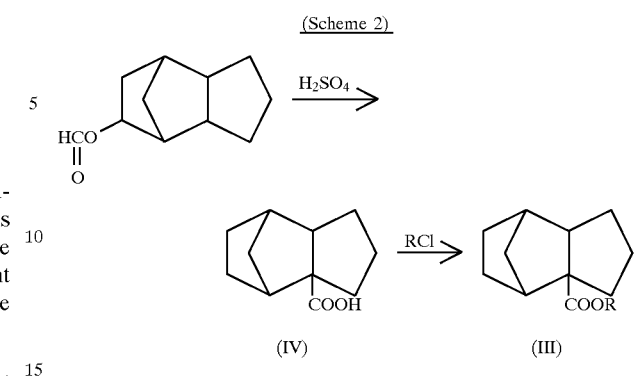

(Scheme 2)

In the above schemes 1 and 2, R is an alkyl group having 1 to 3 carbon atoms.

However, there is a problem in the Koch carboxylation reaction shown by the scheme 1 that equipment for absorbing unreacted carbon monoxide is necessitated because there is a necessity to supply carbon monoxide in an excessively great amount to starting materials, and unreacted carbon monoxide is discharged in a gaseous state, and that there is danger in its operation because carbon monoxide is highly toxic gas. Also, there is a problem in the Koch reaction that the amount of acid used is extremely great, i.e. not less than 10 moles per mole of dihydrodicyclopentadiene is necessitated. According to the method employing the reaction shown by the scheme 2 with a formate, although the amount of acid used is decreased to 6 moles, this method remains unsatisfactory. The acid used in these methods is unrecoverable in some cases. In such cases, disposal of a large amount of waste acid arises a major process problem. Thus, it has been desired that a new industrially useful method for preparing the compound (III) is developed.

DISCLOSURE OF INVENTION

Accordingly, it is an object of the present invention to provide an industrially advantageous method for preparing tricyclo[$5.2.1.0^{2,6}$]decane-2-carboxylate represented by the formula (III).

It is another object of the present invention to provide tricyclo[$5.2.1.0^{2,6}$]deca-8-ene-2-carboxylate represented by the formula (I), which is a novel and important compound as a starting material for the preparation of tricyclo[$5.2.1.0^{2,6}$]decane-2-carboxylate represented by the formula (III).

It is still another object of the present invention is to provide a method for preparing tricyclo[$5.2.1.0^{2,6}$]deca-8-ene-2-carboxylate.

These and other objects of the present invention will be apparent from the following description.

In one embodiment, the present invention relates to a tricyclo[$5.2.1.0^{2,6}$]deca-8-ene-2-carboxylate represented by the formula (I):

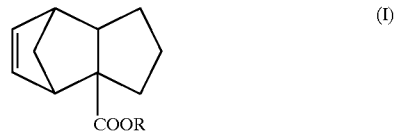

wherein R is an alkyl group having 1 to 3 carbon atoms.

In another embodiment, the present invention relates to a method for preparing a tricyclo[$5.2.1.0^{2,6}$]deca-8-ene-2-carboxylate represented by the formula (I):

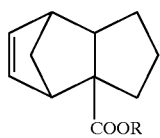

wherein R is an alkyl group having 1 to 3 carbon atoms, comprising the step of reacting a cyclopentenylcarboxylate represented by the formula (II):

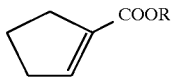

wherein R is as defined above, with cyclopentadiene.

In still another embodiment, the present invention relates to a method for preparing a tricyclo[5.2.1.0$^{2,6}$]decane-2-carboxylate represented by the formula (III):

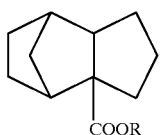

wherein R is an alkyl group having 1 to 3 carbon atoms, comprising the step of reducing, at a double bond, a tricyclo [5.2.1.0$^{2,6}$]deca-8-ene-2-carboxylate represented by the formula (I):

wherein R is as defined above.

In still another embodiment, the present invention relates to a perfume comprising a tricyclo[5.2.1.0$^{2,6}$]deca-8-ene-2-carboxylate represented by the formula (I):

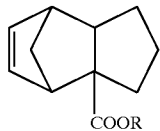

wherein R is an alkyl group having 1 to 3 carbon atoms.

BRIEF DESCRIPTION OF DRAWING

FIG. 1 is a chart showing the results of gas chromatography of a reaction product of ethyl cyclopentenylcarboxylate with dicyclopentadiene obtained in Example 4.

BEST MODE FOR CARRYING OUT THE INVENTION

The present invention is described in detail below.

The tricyclo[5.2.1.0$^{2,6}$]deca-8-ene-2-carboxylate of the present invention is a novel compound which is represented by the formula (I):

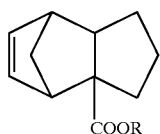

wherein R is an alkyl group having 1 to 3 carbon atoms.

Examples of R are methyl group, ethyl group, n-propyl group and isopropyl group. In the present invention, a preference is given to ethyl group.

It is thought that the compound represented by the formula (I) can be prepared by esterifying the corresponding carboxylic acid represented by the formula (VI):

as shown by the following formula:

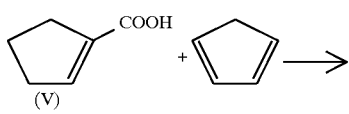

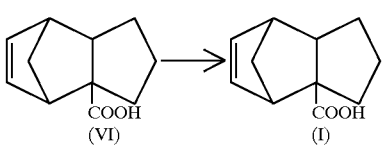

However, the Diels-Alder reaction does not proceed between cyclopentenylcarboxylic acid represented by the formula (V):

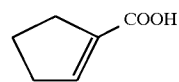

and cyclopentadiene [H. Koch and W. Heaf, Liebigs. Ann. Chem., 638, 111 (1960)], nor is there any other known method for synthesizing the corresponding carboxylic acid represented by the formula (VI). Therefore, it has hitherto been thought that tricyclo[5.2.1.0$^{2,6}$]deca-8-ene-2-carboxylate represented by the formula(I) cannot be prepared from the corresponding carboxylic acid represented by the formula (VI).

It has been unexpectedly found that tricyclo[5.2.1.0$^{2,6}$] deca-8-ene-2-carboxylate represented by the formula (I), which has never been prepared, can be easily prepared by the Diels-Alder reaction of cyclopentenylcarboxylate represented by the formula (II):

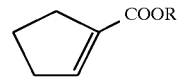

wherein R is as defined above, and cyclopentadiene. On the basis of the above findings, the present invention has been accomplished.

The cyclopentenylcarboxylate represented by the formula (II) is obtained by reacting 2-alkoxycarbonylcyclopentanol represented by the formula (VIII):

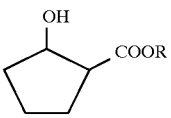

wherein R is as defined above, with p-toluenesulfonyl chloride in a pyridine solvent in accordance with the method described in J. Am. Chem. Soc., 79, 1095 (1957), as shown by the formula:

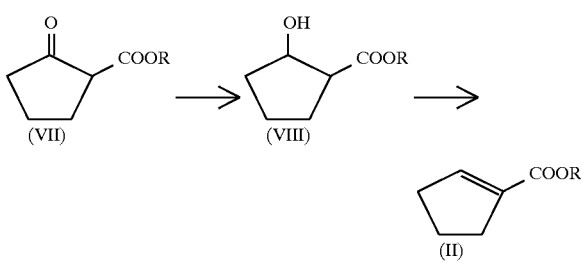

The 2-alkoxycarbonylcyclopentanol represented by the formula (VIII) is obtained by hydrogenating in the presence of Raney nickel catalyst 2-alkoxycarbonylcyclopentanone represented by the formula (VII):

wherein R is as defined above.

The other starting material used for the present invention is cyclopentadiene, which is obtained by thermally decomposing and distilling commercially available dicyclopentadiene in accordance with the method described in Org. Syntheses Coll., Vol. 4, 238 (1963). As mentioned later in the present specification, dicyclopentadiene can be used as a starting material under particular reaction conditions.

In the present invention, it is desired that the amount of cyclopentadiene is 1 to 10 moles, preferably 1 to 2 moles per mole of the cyclopentenylcarboxylate represented by the formula (II) from the viewpoint of suppression of side reactions.

In the present invention, a solvent is not essential, and the reaction can be carried out in the absence of a solvent. When a solvent is used, there is particularly no limitation as to the kind of the solvent, and the reaction proceeds in the presence of various organic solvents. Useful organic solvents include, for example, polar solvents, such as dimethylformamide, dimethylacetamide, 1,3-dimethyl-2-imidazolidinone, dimethyl sulfoxide, dichloromethane, dichloroethane, chloroform, diethyl ether and tetrahydrofuran; and non-polar solvents, such as hexane, benzene, toluene and xylene. From the viewpoint of reaction rate, the use of a polar solvent is preferred. Although the amount of the above solvent is not particularly limited, it is desired that the amount of the solvent is 0.5 to 10 times the weight of the starting cyclopentenylcarboxylate represented by the formula (II), preferably 0.5 to 3 times from the viewpoint of economy. When this reaction is employed, a catalytic effect is exhibited as in the case of common Diels-Alder reaction, especially at low temperatures, more specifically at a temperature of −78° to 50° C.

As a catalyst, there can be used, for instance, catalysts which are generally used in the Diels-Alder reaction, including Lewis acids such as $TiCl_4$, $LiCl_4$, $Ti(OR')_4$ in which R' is an alkyl group having 2 to 4 carbon atoms, $AlCl_3$, $SnCl_4$, $ZnCl_2$, $ZnBr_2$, $Sc(OTf)_3$ and $Y(OTf)_3$; solid acids such as active clay, cation exchange resin and Nafione-H; Lithium salts such as LiX in which X is Cl, Br or I, $Li_2CO_3$ and $LiClO_4$. Among these catalysts, Lewis acids are preferred, with a greater preference given to $TiCl_4$, $AlCl_3$, $SnCl_4$, $Sc(OTf)_3$, and the like.

When a Lewis acid is used as a catalyst, it is desirable to employ a solvent which does not inactivate the Lewis acid, such as dichloromethane and dichloroethane. The amount of the catalyst used is usually 0.01 to 2 moles, preferably 0.05 to 1 mole per mole of the starting cyclopentenylcarboxylate represented by the formula (II).

This reaction can be carried out over a wide temperature range from −78° to 250° C. depending on the reaction conditions employed.

In the absence of a catalyst, it is preferable from the viewpoint of reaction rate that the reaction is carried out at a temperature of not lower than 100° C. Also, from the viewpoint that the reaction is carried out while generating cyclopentadiene by the thermal decomposition of dicyclopentadiene in the reaction solution, it is desired that the reaction is carried out at a temperature of not lower than 150° C. Moreover, it is preferable that the reaction is carried out at a temperature ranging from 150° to 220° C. from the viewpoint of reaction selectivity. In this case, the reaction is preferably carried out in a closed vessel to prevent the volatilization of the resulting low-boiling cyclopentadiene.

When a catalyst is used, the reaction is preferably carried out at a temperature of not higher than 50° C. from the viewpoint of suppression of side reactions, and more preferably at −20° to 25° C. from the viewpoint of reaction rate and suppression of cyclopentadiene polymerization.

In the present invention, the reaction may be carried out using dicyclopentadiene in place of cyclopentadiene. When the dicyclopentadiene is used, cyclopentadiene can be prepared by the thermal decomposition of dicyclopentadiene in the reaction system. In this case, the reaction proceeds in the same manner as in the case where cyclopentadiene is used. Also, there can be used the same solvents and acid catalysts as those used in the reaction using cyclopentadiene. This mode is industrially advantageous in terms of productivity because there is no necessity to previously prepare cyclopentadiene from dicyclopentadiene.

In the present invention, it is desired that the reaction is carried out with adding dropwise cyclopentadiene or dicyclopentadiene to the starting materials containing the cyclopentenylcarboxylate represented by the formula (II) from the viewpoint of suppression of the side reactions such as cyclopentadiene polymerization and the reaction of the carboxylate represented by the formula (I) with cyclopentadiene. It is desired that the dropwise addition rate is 0.05 to 2 moles, preferably 0.2 to 0.5 moles per mole of the cyclopentenylcarboxylate represented by the formula (II) per hour.

The carboxylate represented by the formula (I) obtained by the above reaction is a mixture of the endo- and exoforms. A desired product can be isolated by conventional methods. For example, when the Lewis acid exists, the reaction can be terminated by the addition of aqueous hydrochloric acid, and then the reaction mixture is extracted with ether. The ether layer is sequentially washed with aqueous sodium hydrogencarbonate and with saline solution, and dried. Then, the solvent is distilled away to obtain an oily substance. An objective compound can be isolated by column chromatography. The mixture of the endo- and exo-forms can be directly reduced to the carboxylate represented by the formula (III):

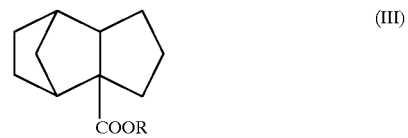

wherein R is as defined above, and the resulting reduced mixture can be used as a material for perfume. If the separation of the endo- and exo-forms is necessitated, they can be separated from each other by fractional distillation, and the like.

The method for preparing tricyclo[5.2.1.0$^{2,6}$]decane-2-carboxylate represented by the formula (III) by reducing the carboxylate represented by the formula (I) is not limited as long as the target site of reduction is a carbon-carbon double bond. It is preferred, for example, that a carbon-carbon double bond is hydrogenated by a chemical method such as catalytic reduction using, for example, platinum black, Raney nickel or Pd/C as a catalyst.

According to the present invention, a novel carboxylate represented by the formula (I), which is a precursor of the carboxylate represented by the formula (III), can be efficiently prepared, thereby the production of the carboxylate represented by the formula (III) is markedly improved in terms of simplicity and productivity, as compared with the conventional methods using the Koch carboxylation reaction. Moreover, the carboxylate represented by the formula (I) can be used as a perfume itself.

The carboxylate represented by the formula (I) has excellent fragrance and is useful as a perfume material. The fragrance of this compound is roughly classified as "fruity-woody." There are two isomers for the carboxylate represented by the formula (I) as shown below:

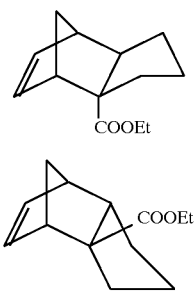

The isomers (A) and (B) have a little different fragrance. Specifically, the isomer (A) has a fragrance of "woody-fruity-spicy-herbal" and the isomer (B), "fruity-floral."

The present invention is hereinafter described in more detail by means of the following examples, which are not to be construed as limitative.

EXAMPLE 1

One gram of ethyl cyclopentenylcarboxylate was added dropwise to 3 ml of a dichloromethane solution of TiCl$_4$ containing 1.35 g of TiCl$_4$, while the solution was stirred at 20° C. in a nitrogen atmosphere. After 30-minute stirring, 2.85 g of cyclopentadiene was added dropwise to the reaction mixture over a period of 4 hours. Then, the reaction was terminated by the addition of a 5% aqueous HCl solution, followed by ether extraction. The ether layer was washed with a saturated aqueous solution of sodium hydrogencarbonate and saturated saline solution, after which it was dried with anhydrous magnesium sulfate. After the solvent was distilled off under reduced pressure, the reaction product was isolated by column chromatography to yield 0.78 g of ethyl tricyclo[5.2.1.0$^{2,6}$]deca-8-ene-2-carboxylate (0.45 g of unreacted ethyl cyclopentenylcarboxylate was recovered). The yield was 54.1% based on the amount of ethyl cyclopentenylcarboxylate, and the conversion ratio, 55.0%. The endo-form/exo-form ratio was 38/62. Physical properties thereof are as follows.

$^1$H-NMR(CDCl$_3$ solvent, TMS internal standard) δ(ppm): endo-form: 1.10 (1H, m), 1.23(3H, t, J=7 Hz), 1.37–1.96 (7H, m), 2.45(2H, br), 2.83(1H, br), 4.06(2H, q, J=7 Hz), 6.07(1H, d—d, J=5 Hz, 3 Hz), 6.18(1H, d-d, J=5 Hz, 3 Hz); exo-form: 1.10(1H, m), 1.26(3H, t, J=7 Hz), 1.35(1H, m), 1.59–1.83(6H, m), 2.77(1H, br), 3.08(1H, m), 3.14(1H, br), 4.16(2H, q, J=7 Hz), 6.18(1H, d-d, J=5 Hz, 3 Hz), 6.25(1H, d-d, J=5 Hz, 3 Hz) IR(neat)ν(cm$^{-1}$): 2964, 1728, 1448, 1302, 1248, 1228, 1176, 1032, 718 MS: 207(M$^+$+1), 141

EXAMPLE 2

The same procedures as in Example 1 were carried out except that 950 mg of AlCl$_3$ was used as a catalyst in place of 1.35 g of TiCl$_4$. The amount 2.85 g of cyclopentadiene was added dropwise to 1 g of ethyl cyclopentenylcarboxylate to give 0.75 g of tricyclo[5.2.1.0$^{2,6}$]deca-8-ene-2-carboxylate. The yield was 50.5% based upon ethyl cyclopentenylcarboxylate, and the conversion ratio, 52.0%. The endo-form/exo-form ratio was 40/60.

EXAMPLE 3

The amount 32 g of ethyl cyclopentenylcarboxylate was placed in an autoclave and heated up to 200° C. to which 47 g of dicyclopentadiene was added dropwise over 4-hour period with stirring. Then, the reaction mixture was cooled to room temperature.

The reaction mixture was distilled to isolate 18.2 g of ethyl tricyclo[5.2.1.0$^{2,6}$]deca-8-ene-2-carboxylate. The yield was 39.1% based upon the amount of ethyl cyclopentenylcarboxylate, and the conversion ratio, 56.0%. The endo-form/exo-form ratio was 37/63.

EXAMPLE 4

The same procedures as in Example 3 were carried out except that 32 g of 1,3-dimethyl-2-imidazolidinone was used as a solvent. A sample of the resulting reaction mixture thus cooled was subjected to gas chromatography under the following conditions:

Column: Ultra-1(Cross-Linked Methyl Siloxane)

25 m×0.2 mm×0.33 μm

Oven: 100° C. (0 min) to 280° C. (5 min) at 5° C./min

Injection: 1 μl spilit mode (spilit ratio 100:1)

Inlet at 280° C.

Detector: FID (280° C.)

The results of the gas chromatography are shown in FIG. 1.

As is obvious from the chart shown in FIG. 1, the above compound contains ethyl tricyclo[5.2.1.0$^{2,6}$]deca-8-ene-2-carboxylate in a high content.

In the chart shown in FIG. 1, the marks "a" to "1" denote as follows:

a:

(CH$_3$CH$_2$)$_2$O (Solvent)

b:

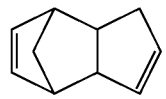

c:

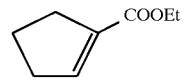

d:

-continued

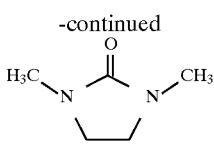

e:

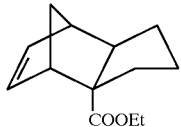

f:

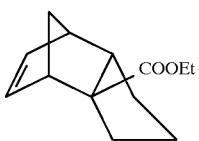

g:

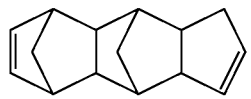

h:

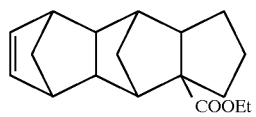

i:

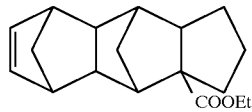

j:

k:

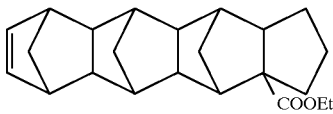

l:

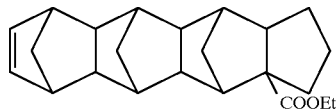

The yield was 35.8% based upon the amount of ethyl cyclopentenylcarboxylate, and the conversion ratio, 42.2%. The endo-form/exo-form ratio was 40/60.

EXAMPLE 5

The amount 1.3 g of 5%-Pd/C (with 50% moisture content) was added to 13.1 g of ethyl tricyclo[5.2.1.0$^{2,6}$] deca-8-ene-2-carboxylate obtained in the same procedures as in Example 1. The resultant mixture was stirred at 50° C. for 5 hours under hydrogen pressure of 5 kg/cm$^2$. After the catalyst was removed by filtration, the filtrate was distilled to yield 12.3 g of ethyl tricyclo[5.2.1.0$^{2,6}$]decane-2-carboxylate. The yield was 93.0%.

The product thus obtained was an excellent perfume component, having fruity and woody fragrance.

INDUSTRIAL APPLICABILITY

The method of the present invention industrially and advantageously provides tricyclo[5.2.1.0$^{2,6}$]decane-2-carboxylate. Also, the present invention provides tricyclo [5.2.1.0$^{2,6}$]deca-8-ene-2-carboxylate, which is a novel compound suitably used as a starting material for preparation of tricyclo[5.2.1.0$^{2,6}$]decane-2-carboxylate and an industrially advantageous method for producing the compound.

EQUIVALENTS

Those skilled in the art will recognize or be able to ascertain, using no more than routine experimentation, many equivalents to the specific materials and components described herein. Such equivalents are intended to be encompassed in the scope of the following claims:

We claim:

1. A tricyclo[5.2.1.0$^{2,6}$]deca-8-ene-2-carboxylate represented by the formula (I):

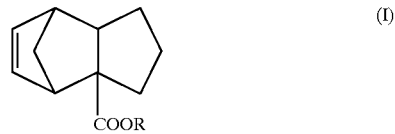

(I)

wherein R is an alkyl group having 1 to 3 carbon atoms.

2. A method for preparing a tricyclo[5.2.1.0$^{2,6}$]deca-8-ene-2-carboxylate represented by the formula (I):

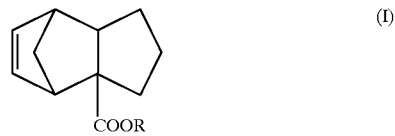

(I)

wherein R is an alkyl group having 1 to 3 carbon atoms, comprising the step of reacting a cyclopentenylcarboxylate represented by the formula (II):

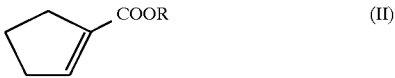

(II)

wherein R is as defined above, with cyclopentadiene.

3. The method according to claim 2, wherein the cyclopentadiene is prepared by the thermal decomposition of dicyclopentadiene in the reaction solution.

4. A method for preparing a tricyclo[5.2.1.0$^{2,6}$]decane-2-carboxylate represented by the formula (III):

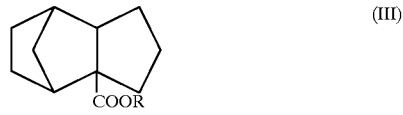

(III)

wherein R is an alkyl group having 1 to 3 carbon atoms, comprising the step of reducing, at a double bond, a tricyclo [5.2.1.0$^{2,6}$]deca-8-ene-2-carboxylate represented by the formula (I):

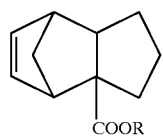
(I)
wherein R is as defined above.
5. A perfume comprising a tricyclo[5.2.1.0$^{2,6}$]deca-8-ene-2-carboxylate represented by the formula (I):
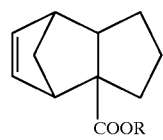
(I)
wherein R is an alkyl group having 1 to 3 carbon atoms.
* * * * *